United States Patent [19]

Fukuda et al.

[11] Patent Number: 4,863,862
[45] Date of Patent: Sep. 5, 1989

[54] MICROBIAL METHOD OF PRODUCING $C_3$ AND/OR $C_4$ HYDROCARBONS

[75] Inventors: Hideo Fukuda, 5-10, Tezukayama-naka 3-chome, Sumiyoshi-ku, Osaka 558; Takahira Ogawa; Takao Fujii, both of Kumamoto, all of Japan

[73] Assignee: Hideo Fukuda, Osaka, Japan

[21] Appl. No.: 225,589

[22] Filed: Jul. 26, 1988

Related U.S. Application Data

[63] Continuation of Ser. No. 636,963, Aug. 2, 1984.

[30] Foreign Application Priority Data

Aug. 4, 1983 [JP] Japan ................................. 58-143457

[51] Int. Cl.$^4$ .......................... C12P 5/00; C12P 5/02; C12N 1/20
[52] U.S. Cl. .................................... 435/166; 435/167; 435/822; 435/911
[58] Field of Search ........................ 435/166, 167, 253

[56] References Cited

U.S. PATENT DOCUMENTS 4,414,329 11/1983 Wegner ................................. 435/68

OTHER PUBLICATIONS

*Bergy's Manual of Determinative Bacteriology* (8th ed., 1974), Buchanan and Gibbons (eds.), (Wilkins & Wilkins, Co., Balt.), p. 328.

Hunt et al., "Formation of $C_4$–$C_7$ Hydrocarbons from Bacterial Degradation of Naturally Occurring Terpenoids", *Nature*, 288:577–578 (Dec. 11, 1980).

Rheinheimer, *Aquatic Microbiology* (2nd ed., John Wiley & Sons), 1980, pp. 33–41.

Boehler–Kohler, "Paraquat–Induced Production of Hydrocarbon Gases", CAS 1982, 97:140157j.

Davis et al. (1954), Science, vol. 119, pp. 381–382, "Detection of Microbially Produced Gaseous Hydrocarbons Other Than Methane".

*Primary Examiner*—Ronald W. Griffin
*Assistant Examiner*—Pamela S. Webber
*Attorney, Agent, or Firm*—Burgess, Ryan & Wayne

[57] ABSTRACT $C_3$ and/or $C_4$ hydrocarbons(s) is produced by the aerobic cultivation of a microorganism belonging to a wide variety of genera of Fungi, Yeasts, Bacteria and Actinomycetes. Industrial wastes and various biomass can be employed as nutrient source in the cultivation.

5 Claims, No Drawings

MICROBIAL METHOD OF PRODUCING C₃ AND/OR C₄ HYDROCARBONS

This application is a continuation of application Ser. No. 636,963, filed Aug. 2, 1984.

This invention relates to a microbial method of producing $C_3$ and/or $C_4$ hydrocarbons. In accordance with the production method of this invention, there can be obtained useful lower hydrocarbons such as propane, propylene, n-butane, isobutane, 1-butene, isobutene, trans-2-butene, cis-2-butene, and the like by means of microorganisms.

These hydrocarbons occur in petroleum cracking product gases and natural gases, and have been made available from various stages of their purification and fractionation. However, the terrestrial reserves of these materials are limited.

Under the circumstances a study was undertaken of the microbial production route to these hydrocarbons using a reproducible biomass as the main raw material and the instant method conceived.

Regarding the production of propane, propylene, butane and butene by microorganisms, there is a report that methane as well as trace amounts of ethane, propane, butane (chemical structures not established) and butene (chemical structures not established) were detected when a mixture of microorganisms in fermented bovine feces (strains not isolated or identified) was anaerobically cultivated [K. G. Gollakota and B. Jayalakshmi: Biochemical and Biophysical Research Communications 110, 32–35 (1983)], a report that small amounts of ethane, ethylene, propane, propylene, and n-butane were formed by mushrooms [E. M. Turner, M. Wright, T. Ward, and D. J. Osborne, J. Gen. Microbiol., 91, 167–176 (1975)] and a report that small amounts of ethane, ethylene, propane and propylene were detected in unaerobic methane fermentation with a mixture of microorganisms contained in bovine feces (strains not isolated or identified) and on agar plate culture of *Penicillium digitatum* ATCC 10030 [J. B. Davis and R. M. Squires: Science, 119, 381–382 (1954)]. However, according to these reports, the yields of hydrocarbons are invariably small, the processes are either anaerobic culture or solid surface culture, and either the microorganisms involved are indefinite or the chemical structure of product hydrocarbons are not identified.

This invention provides a microbial method of producing a hydrocarbon product having carbon numbers of 3 and/or 4 which comprises culturing aerobically a strain of microorganism capable of producing $C_3$ and/or $C_4$ hydrocarbon(s) to thereby cause the formation of said hydrocarbon(s), and recovering the hydrocarbon(s) therefrom.

The microorganisms which can be employed in accordance with the present invention are fungi belonging to the genera Phytophthora, Mucor, Rhizopus, Absidia, Mortierella, Cunninghamella, Taphrina, Monascus, Nectria, Gibberella, Chaetomium, Neurospora, Monilia, Trichoderma, Aspergillus, Paecilomyces, Gliocladium, Sporotrichum, Microsporum, Trichophyton, Cladosporium, Syncephalastrum and Phycomyces, inclusive of mutant strains thereof; yeasts belonging to the genera Endomyces, Schizosaccharomyces, Saccharomyces, Pichia, Hansenula, Debaryomyces, Saccharomycopsis, Rhodotorula, Sporobolomyces, Cryptococcus, Candida and Brettanomyces, inclusive of mutant strains thereof; bacteria belonging to the genera Bacillus, Brevibacterium, Corynebacterium, Micrococcus, Paracoccus, Proteus, Pseudomonas, Salmonella, Serratia and Acetobacter, inclusive of mutant strains thereof; and actinomycetes belonging to the genera Streptomyces, Actinomyces, Amorphosporangium and Intrasporangium, inclusive of mutant strains thereof.

Of these microorganisms, the following strains are representative of the organisms capable of producing these hydrocarbons in substantial quantities.

FUNGI: *Phytophthora capsici* IFO-8386, *Mucor hiemalis f. corticolus* IFO-9401, *Mucor hiemalis f. hiemalis* IFO-9404 and IFO-9405, *Mucor hiemalis f. luteus* IFO-9410 and IFO-9411, *Rhizopus javanicus* IFO-5441, *Rhizopus japonicus* IFO-4758, *Absidia cylindrospora* IFO-4000, *Mortierella isabellina* IFO-8183, *Mortierella elongata* IFO-8570, *Cunninghamella elegans* IFO-4441, *Taphrina caerulescens* IFO-9242, *Taphrina wiesneri* IFO-7776, *Monascus anka* IFO-6540, *Monascus albidus* IFO-4489, *Nectria flammea* IFO-9628, *Gibberella fujikuroi* IFO-5268, *Chaetomium globosum* IFO-6347, *Neurospora crassa* IFO-6067, *Monilia geophila* IFO-5425, *Trichoderma viride* IFO-4847, *Aspergillus clavatus* IFO-4045, IFO-8605 and IFO-8606, *Paecilomyces carneus* IFO-8292, *Paecilomyces elegans* IFO-6619, *Gliocladium aureum* IFO-9055, *Gliocladium deliquescens* IFO-7062, *Gliocladium roseum* IFO-7063, *Sporotrichum aureum* IFO-9381, *Microsporum gypseum* IFO-5948, *Trichophyton mentagrophytes* IFO-5466, *Cladosporium resinae* IFO-8588, *Syncephalastrum racemosum* IFO-4816 and *Phycomyces nitens* IFO-9422.

YEASTS: *Endomyces geotrichum* IFO-9541, *Endomyces reessii* IFO-1112, *Endomyces magnusii* IFO-0110, *Schizosaccharomyces octosporus* IFO-0353, *Schizosaccharomyces pombe* IFO-0340, *Schizosaccharomyces japonicus* IFO-1609, *Saccharomyces bailii* IFO-0468, Saccharomyces sp. IFO-2363, IFO-2226, IFO-2112, IFO-2115, IFO-2342, IFO-2343, IFO-2344, IFO-2345, IFO-2346, IFO-2347 and IFO-2376, *Pichia acaciae* IFO-1681, *Pichia besseyi* IFO-1707, *Pichia farinosa* IFO-0459, *Hansenula capsulata* IFO-0721, *Debaryomyces nepalensis* IFO-1428, *Saccharomycopsis lipolytica* IFO-1658, *Saccharomycopsis crataegensis* IFO-1708, *Saccharomycopsis fibuligera* IFO-1745, *Rhodotorula glutinis* IFO-0697 and IFO-1501, *Rhodotorula minuta* IFO-0387, *Sporobolomyces salmonicolor* IFO-0374, *Sporobolomyces pararoseus* IFO-0376, *Cryptococcus albidus* IFO-0378 and IFO-0939, *Cryptococcus flavus* IFO-0407, *Cryptococcus laurentii* IFO-0384, *Candida albicans* IFO-1060, *Candida butyri* IFO-1571, *Candida guilliermondii* IFO-0454, *Brettanomyces bruxellensis* IFO-0628 and *Brettanomyces intermedius* IFO-1587.

BACTERIA: *Bacillus circulans* IFO-3329, *Bacillus coagulans* IFO-3557, *Bacillus pumilus* IFO-3813, *Bacillus subtilis* IFO-3023, *Brevibacterium ammoniagenes* ATCC-6872, *Brebibacterium lactofermentum* ATCC-13655, *Corynebacterium aquaticum* IFO-12154, *Corynebacterium fascience* IFO-12077, *Corynebacterium paurometabolum* IFO-12160, *Micrococcus luteus* IFO-3064, *Paracoccus denitrificans* IFO-12442, *Proteus mirabilis* IFO-3849, *Pseudomonas aeruginosa* IFO-3445, *Pseudomonas putida* IFO-3738, *Pseudomonas stutzeri* IFO-3773, *Salmonella typhimurium* IFO-12529, *Serratia marcescens* IFO-12648 and *Acetobacter aceti* IFO-3281.

ACTINOMYCETES: *Streptomyces flaveolus* IFO-3408, *Streptomyces fradiae* IFO-3360, *Streptomyces lavendulae* IFO-3145 and IFO-13709, *Streptomyces viridochromogenes* IFO-3113, *Streptomyces regensis* IFO-13448, *Actinomyces aurigineus* IFO-13022, *Actinomyces*

*vulgaris* IFO-13107, *Amorphosporangium auranticolor* IFO-12245, and *Intrasporangium calvum* IFO-12989.

In addition to these strains, many strains of the genera mentioned have been found to produce hydrocarbons.

The culture of the strains in this invention may be carried out by liquid or solid culture employing a liquid or solid medium. If desired, the liquid medium may be contacted with the strains fixed in a suitable carrier in the form of bioreactor.

The culture medium used for cultivation of such microorganisms may be the conventional medium for culture of fungi, yeasts, bacteria or actinomycetes, which contains carbon sources, nitrogen sources, inorganic salts, and other nutrients.

Thus, various carbohydrates such as glucose, sucrose, maltose, starch, xylose, sorbitol, etc., alcohols such as glycerol, ethanol, etc., organic acids such as acetic acid and other fatty acids, and crude materials containing them may be used as carbon sources. The main raw materials which are particularly useful for the purposes of this invention are reproducible biomass which are either naturally occurring or available artificially as byproducts, such as materials from agricultural, forestal, fisheries and live-stock industry activities, industrial waste water, various industrial wastes, and active sludges from the biological treatment of public sewage, plant effluents or raw sewage. Though it depends on the strains of organisms used, these materials are preliminarily dissolved, decomposed or otherwise pretreated as necessary.

As nitrogen sources, there can be advantageously used ammonia gas, aqueous ammonia and ammonium salts. When a biomass is used as the main raw material, the addition of such nitrogen sources may not be essential.

As inorganic salts, phosphates, potassium salts, magnesium salts, sodium salts, calcium salts, etc. can be routinely employed, although these may be dispensed with when a biomass is employed.

The addition of vitamins and amino acids or of materials containing them such as yeast extract, peptone, meat extract, corn steep liquor, and the like may contribute to accelerated growth of the strain used or improved yields of desired hydrocarbons.

The cultivation of microorganisms is carried out under aerobic conditions, for example by aerated stirring or stationary culture, with the pH and temperature being controlled at pH 2 to 9 and a temperature of 20° to 45° C., respectively. Thus, for each strain, the optimum pH and temperature are selected. As the cultivation is conducted for 1 to 10 days, a biogas containing a significant amount of $C_3$ and/or $C_4$ hydrocarbon is produced.

The hydrocarbon content of the product biogas is assayed as follows.

A x=1 to 5 ml portion of the broth in the course of cultivation or at the end of cultivation is taken into a test tube with a total volume of V=10–50 ml and after closure with a sterile rubber stopper, the broth is incubated on a reciprocating shaker at 20° to 45° C. for t=1–7 hours. Since the respiration rate varies with different strains, it is preferable to vary the parameters V, x and t so as to prevent oxygen deficiency during shaking.

After the reciprocal shaking, y=0.1 to 2 ml of the gas is taken from the top plenum of the test tube using a gas syringe and subjected to the conventional FID gas chromatography using nitrogen gas as the carrier gas. (The optimum column temperature is used according to the type of the column packing. The injection temperature is also varied accordingly.)

Preferred examples of the column packing material are Porapak Q, X-28, Bond-GC/PIC, and activated alumina, and a suitable packing material is selected according to the type of hydrocarbon. Separately, standards of various hydrocarbons are prepared and subjected to gas chromatography under the above conditions by the same procedure to measure the retention times of the hydrocarbons on the recording paper. The calibration curves of hydrocarbons are also constructed using the standards.

Referring to the gas chromatogram of the above test gas, the retention times of the peaks on the recording paper are measured and compared with those of said standards to identify the corresponding hydrocarbons. Then, the area of the fraction corresponding to each hydrocarbon is measured and the amount $Ei^{nl}$ of the hydrocarbon is calculated by reference to the calibration curve of the standard gas.

The rate of production $Pi^{nl}$/ml.hr of each hydrocarbon in the test gas can be calculated by means of the following equation. The subscript i means one of $C_3$ and/or $C_4$ hydrocarbons.

$$Pi = Ei \cdot \left(\frac{V-x}{y}\right) \cdot \frac{1}{x} \cdot \frac{1}{t}$$

To separate the $C_3$ and/or $C_4$ hydrocarbon from the product biogas, the biogas is either adsorbed on a suitable adsorbent such as zeolite or activated carbon or contacted with a sodium hydroxide solution to remove the byproduct carbon dioxide gas and, then, adsorbed on the above-mentioned adsorbent, followed by desorption. The zeolite may for example be Molecular Sieves 3A, 4A, 5A and 10X [Union Showa K. K.] or Zeoram A-3, A-4, A-5 or F-9 [Toyo Soda Industries, Ltd.]. The activated carbon may for example be Molecular Sieving Carbon [Takeda Chemical Industries, Ltd.].

The present invention is characterized in that the readily-available, reproducible biomass, particularly the waste resources from agricultural, forestal, fisheries and livestock industry, industrial waste water, industrial wastes, sludges available from the biological treatment of public sewage, factory wastes, or raw sewage can be advantageously utilized as main raw materials and that practicing the present invention is tantamount to a microbiological disposal of wastes and effluents. Furthermore, the method according to the present invention is advantageous over the conventional methods in that the main raw material is a reproducible biomass which will be never be depleted, the production is acomplished under mild conditions such as low temperature and low pressure because of its being a microbiological process, and the impurity gases are mostly carbon dioxide. As the results, the purification of hydrocarbon is easy and the purity of product is high.

The following examples are further illustrative of this invention.

EXAMPLE 1

Fifty ml of the medium indicated in Table 1 was added to each conical flask of 300 ml capacity and after steam sterilization by autoclaving at 120° C. for 15 minutes, a loopful of one of precultured strains was incubated to each flask. The flasks were incubated on a reciprocating shaker (for bacteria; stroke 7 cm, 120 cpm) or a rotary shaker (for fungi, yeasts, and actinomycetes; radius 7 cm, 180 rpm) at 25° C. (for fugi, yeasts, and actinomycetes) or 30° C. (for bacteria) for 1 to 2 days (bacteria), 2 to 3 days (yeasts), 4 to 7 days (fungi), or 3 to 7 days (actinomycetes).

A 1 to 2 ml of the culture thus prepared was taken into a sterile test tube of 34 ml capacity and after hermetic closure, incubated on a reciprocating shaker at 25° C. (fungi, yeasts and actinomycetes) or 30° C. (bacteria) for 5 to 10 hours so as to cause evolution of a biogas.

After shaking, a 1 ml portion of the plenum gas was taken from each test tube with a gas syringe and subjected to gas chromatography and calculated as set forth in the text. The results are shown in Table 2.

TABLE 1

Composition of media for various microorganisms

| Compositions | Fungi | Yeasts | Bacteria | Actinomycetes |
|---|---|---|---|---|
| | CSL | NB | NB | NB | NB |
| Glucose | 40 g/l | 20 g/l | 20 g/l | 20 g/l | 20 g/l |
| Polypepton* | — | 5 g/l | 5 g/l | 5 g/l | 5 g/l |
| Meat extract | — | 3 g/l | 3 g/l | 3 g/l | 3 g/l |
| Yeast extract | — | 2 g/l | 2 g/l | 2 g/l | 2 g/l |
| Corn steep liquor (CSL) | 40 g/l | — | — | — | — |
| Sodium chloride | — | 2 g/l | 2 g/l | 2 g/l | 2 g/l |
| Calcium carbonate | 3.5 g/l | — | — | — | — |
| Sodium nitrate | 3.0 g/l | — | — | — | — |
| Dipotassium phosphate | 0.5 g/l | — | — | — | — |
| Magnesium sulfate (7H$_2$O) | 0.25 g/l | — | — | — | — |
| Initial pH (adjusted with sodium hydroxide or hydrochloric acid) | 5.0 | 6.0 | 6.0 | 7.0 | 7.0 |

*Product of Daigo Eiyo K.K., Osaka, Japan.

TABLE 2

Production rate of C$_3$ or/and C$_4$ hydrocarbons by various strains
(Unit of numerals in the Table: nl/ml. hr)

| Name of strain | | C$_3$ | | C$_4$ | | | | |
|---|---|---|---|---|---|---|---|---|
| | | Propane | Propylene | i-Butane | n-Butane | 1-Butene | i-Butene | trans-2-Butene | cis-2-Butene |
| (Fungi) | | | | | | | | | |
| Phytophthora capsici | IFO-8386 | 0.1 | | | 0.1 | | 0.2 | | |
| Mucor hiemalis f. corticolus | IFO-9401 | 0.1 | | | | | 0.1 | | |
| Mucor hiemalis f. hiemalis | IFO-9404 | 0.9 | | | | | | | |
| Mucor hiemalis f. hiemalis | IFO-9405 | 0.5 | | | | | | | |
| Mucor hiemalis f. luteus | IFO-9410 | 0.4 | | | | | | | |
| Mucor hiemalis f. luteus | IFO-9411 | | | | | | 0.1 | | |
| Rhizopus javanicus | IFO-5441 | 0.2 | 0.1 | | 0.2 | | 0.5 | | |
| Rhizopus japonicus | IFO-4758 | 0.8 | 0.1 | | 0.1 | | | | |
| Absidia cylindrospora | IFO-4000 | 0.8 | | | | | | | |
| Mortierella isabellina | IFO-8183 | 0.1 | | | 0.1 | | 0.2 | | |
| Mortierella eleongata | IFO-8570 | 0.6 | | | 0.1 | | | 0.1 | |
| Cunninghamella elegans | IFO-4441 | 0.6 | 0.1 | | | | | | |
| Taphrina caerulescens | IFO-9242 | 0.6 | | | | | | | |
| Taphrina wiesneri | IFO-7776 | 0.2 | | | 0.2 | 0.5 | 0.5 | | |
| Monascus anka | IFO-6540 | 0.4 | | | | | | | |
| Monascus albidus | IFO-4489 | 0.4 | | | | | | | |
| Nectria flammea | IFO-9628 | 1.2 | | | 0.6 | | | | |
| Gibberella fujikuroi | IFO-5268 | 0.1 | | | 0.1 | | 0.2 | | |
| Chaetomium globosum | IFO-6347 | | | | 0.1 | | 0.1 | | 0.2 |
| Neurospora crassa | IFO-6067 | 0.4 | | | | | | | |
| Monilia geophila | IFO-5425 | 0.8 | | | | | | | |
| Trichoderma viride | IFO-4847 | 1.0 | | | | | | 0.1 | |
| Aspergillus clavatus | IFO-4045 | 0.7 | | | | | | | |
| Aspergillus clavatus | IFO-8605 | 2.3 | | | | | | | |
| Aspergillus clavatus | IFO-8606 | 0.6 | | | | | | | |

TABLE 2-continued

Production rate of $C_3$ or/and $C_4$ hydrocarbons by various strains
(Unit of numerals in the Table: nl/ml. hr)

| Name of strain | | $C_3$ | | $C_4$ | | | | | |
|---|---|---|---|---|---|---|---|---|---|
| | | Propane | Propylene | i-Butane | n-Butane | 1-Butene | i-Butene | trans-2-Butene | cis-2-Butene |
| *Paecilomyces carneus* | IFO-8292 | 0.2 | | | 0.2 | | 0.4 | | |
| *Paecilomyces elegans* | IFO-6619 | 1.0 | | 0.1 | 0.1 | | | | |
| *Gliocladium aureum* | IFO-9055 | 0.9 | | 0.1 | 0.7 | | | 0.1 | |
| *Gliocladium deliquescens* | IFO-7062 | 0.1 | | | 0.1 | | 0.6 | | |
| *Gliocladium roseum* | IFO-7063 | | 3.0 | | | 0.3 | | | |
| *Sporotrichum aureum* | IFO-9381 | 0.5 | | | | | 0.5 | | |
| *Microsporum gypseum* | IFO-5948 | 0.2 | | 0.1 | 0.1 | | 0.2 | | |
| *Trichophyton mentagrophytes* | IFO-5466 | | | | | | 0.1 | | |
| *Cladosporium resinae* | IFO-8588 | 0.2 | | | 0.1 | | 0.5 | | |
| *Syncephalastrum racemosum* | IFO-4816 | 0.1 | 0.2 | | 0.1 | 0.1 | 0.2 | | |
| *Phycomyces nitens* | IFO-9422 | 0.1 | | | 0.1 | | 0.3 | | |
| (Yeasts) | | | | | | | | | |
| *Endomyces geotrichum* | IFO-9541 | 1.0 | | | 0.1 | | 0.2 | | |
| *Endomyces reessii* | IFO-1112 | 1.0 | | | | 0.1 | 0.6 | | |
| *Endomyces magnusii* | IFO-0110 | 0.5 | 0.1 | | | | | | |
| *Schizosaccharomyces octosporus* | IFO-0353 | 0.1 | 1.2 | | 0.1 | | 0.5 | | |
| *Schizosaccharomyces pombe* | IFO-0340 | 0.1 | | | 0.1 | | | | |
| *Schizosaccharomyces japonicus* | IFO-1609 | 0.1 | | | | | | | |
| *Saccharomyces bailii* | IFO-0468 | 0.2 | 0.1 | | | | | | |
| *Pichia acaciae* | IFO-1681 | 0.1 | 0.1 | | 0.1 | | | | |
| *Pichia besseyi* | IFO-1707 | 0.9 | | 0.1 | 0.1 | 0.1 | 0.1 | | |
| *Pichia farinosa* | IFO-0459 | 0.9 | | 0.1 | 0.2 | | 0.1 | | |
| *Hansenula capsulata* | IFO-0721 | 0.2 | 0.1 | | 0.1 | | | | |
| *Debaryomyces nepalensis* | IFO-1428 | 0.1 | | | 0.1 | | | | |
| *Saccharomycopsis lipolytica* | IFO-1658 | 0.5 | | | 0.1 | | | | |
| *Saccharomycopsis crataegensis* | IFO-1708 | 0.4 | 0.1 | | 0.1 | | 0.1 | | 0.1 |
| *Saccharomycopsis fibuligera* | IFO-1745 | 1.1 | | 0.2 | 0.1 | | 0.1 | | |
| *Rhodotorula glutinis* | IFO-0697 | 0.7 | | 0.1 | | | 0.3 | | |
| *Rhodotorula glutinis* | IFO-1501 | | 0.1 | | | | | | |
| *Rhodotorula minuta* | IFO-0387 | 0.2 | | | | | 1.7 | | |
| *Sporobolomyces salmonicolor* | IFO-0374 | 0.4 | 0.1 | | 0.1 | 0.1 | 0.2 | | |
| *Sporobolomyces pararoseus* | IFO-0376 | 0.3 | | 0.1 | | | 0.3 | | |
| *Cryptococcus albidus* | IFO-0378 | 6.5 | 0.1 | 0.1 | 0.1 | | 0.1 | | |
| *Cryptococcus albidus* | IFO-0939 | 0.1 | | | 0.1 | | 0.1 | | |
| *Cryptococcus flavus* | IFO-0407 | 0.1 | | | 0.1 | 0.2 | | | 0.7 |
| *Cryptococcus laurentii* | IFO-0384 | 0.9 | | 0.1 | 0.1 | | 0.1 | | |
| *Candida albicans* | IFO-1060 | 0.3 | 0.2 | | | | | | |
| *Candida butyli* | IFO-1571 | 1.2 | | | | 0.1 | 0.2 | | |
| *Candida guilliermondii* | IFO-0454 | 0.5 | | | 0.1 | | | | |
| *Brettanomyces bruxellensis* | IFO-0628 | 0.2 | | | 0.1 | | | | |
| *Brettanomyces intermedius* | IFO-1587 | 0.1 | | | | | 0.1 | | |
| *Saccharomyces sp.* | IFO-2363 | 0.3 | 0.2 | | | | 0.2 | | |
| *Saccharomyces sp.* | IFO-2226 | 0.5 | | | | | | | |
| *Saccharomyces sp.* | IFO-2112 | 0.5 | 0.1 | | | | | | |
| *Saccharomyces sp.* | IFO-2115 | 0.5 | 0.1 | | 0.1 | | 0.1 | | |
| *Saccharomyces sp.* | IFO-2342 | 1.3 | | | | 0.1 | | | |
| *Saccharomyces sp.* | IFO-2343 | 0.1 | | | 0.1 | | | | |
| *Saccharomyces sp.* | IFO-2344 | 0.2 | 0.1 | | 0.1 | | 0.2 | | |
| *Saccharomyces sp.* | IFO-2345 | 0.4 | 0.1 | | | | | | |
| *Saccharomyces sp.* | IFO-2346 | 1.1 | | 0.1 | | | | | |
| *Saccharomyces sp.* | IFO-2347 | 0.1 | 0.1 | | | | | | |
| *Saccharomyces sp.* | IFO-2376 | 0.1 | 0.2 | | | | | | |
| (Bacteria) | | | | | | | | | |
| *Bacillus circulans* | IFO-3329 | 0.1 | 0.1 | | 0.1 | 0.2 | | | |
| *Bacillus coagulans* | IFO-3557 | 0.3 | 0.2 | | 0.2 | | | | |
| *Bacillus pumilus* | IFO-3813 | | | | | 0.4 | | | |
| *Bacillus subtilis* | IFO-3023 | | 0.1 | | 0.1 | | | | |
| *Brevibacterium ammoniagenes* | ATCC-6872 | 8.6 | | | 0.2 | | | | |
| *Brevibacterium* | | | | | | | | | |

TABLE 2-continued

Production rate of $C_3$ or/and $C_4$ hydrocarbons by various strains
(Unit of numerals in the Table: nl/ml. hr)

| Name of strain | | $C_3$ | | $C_4$ | | | | | |
|---|---|---|---|---|---|---|---|---|---|
| | | Propane | Propylene | i-Butane | n-Butane | 1-Butene | i-Butene | trans-2-Butene | cis-2-Butene |
| lactofermentum | ATCC-13655 | 0.2 | | 0.1 | | 0.2 | 0.1 | | |
| Corynebacterium aquaticum | IFO-12154 | 0.3 | 0.2 | | 0.2 | | | | |
| Corynebacterium fascians | IFO-12077 | | | 0.1 | 0.7 | | | | |
| Corynebacterium paurometabolum | IFO-12160 | 0.7 | 0.2 | | | | | 0.2 | |
| Micrococcus luteus | IFO-3064 | 2.3 | | 0.1 | 0.1 | | | | |
| Paracoccus denitrificans | IFO-12442 | 0.2 | 0.2 | | | | | | |
| Proteus mirabilis | IFO-3849 | 2.2 | | 0.1 | 0.1 | 0.2 | | | |
| Pseudomanas aeruginosa | IFO-3445 | | | 0.1 | 0.1 | 0.1 | | | |
| Pseudomanas putida | IFO-3738 | | | 0.1 | | | | 0.2 | |
| Pseudomanas stutzeri | IFO-3773 | 2.3 | 0.2 | | | | | | |
| Salmonella typhimurium | IFO-12529 | 2.3 | 0.2 | | | 0.1 | 0.1 | | |
| Serratia marcescens | IFO-12648 | 0.1 | 0.1 | 0.1 | | | | | |
| Acetobacter aceti | IFO-3281 | 0.2 | | | | | | | |
| (Actinomycetes) | | | | | | | | | |
| Streptomyces flaveolus | IFO-3408 | | | | 0.4 | | | 0.2 | |
| Steptomyces fradiae | IFO-3360 | 0.2 | | 0.2 | 0.3 | | | | |
| Streptomyces lavendulae | IFO-3145 | | | 0.2 | 0.2 | | | 0.2 | |
| Streptomyces lavendulae | IFO-13709 | 1.2 | 0.1 | | 0.2 | | | 0.4 | |
| Streptomyces viridochromogenes | IFO-3113 | 0.2 | 0.3 | | 0.1 | | | | |
| Streptomyces regensis | IFO-13448 | 0.2 | 0.1 | 0.1 | | | | | |
| Actinomyces aurigineus | IFO-13022 | | | | 0.1 | | | | |
| Actinomyces vulgaris | IFO-13107 | | 0.1 | | | | | | |
| Amorphosporangium auranticolor | IFO-12245 | | 0.2 | | | | | | |
| Intrasporangium calvum | IFO-12989 | 0.3 | | 0.2 | 0.1 | | | | |

EXAMPLE 2

Fifty ml of excess sludge (about 2.0% solids; about 1.0% organic matter) from a sewage disposal plant was added to each conical flask of 300 ml capacity and subjected to steam sterilization at 120° C. for 15 minutes. After cooling, a loopful of a preculture of *Aspergillus clavatus* IFO 4045 or of *Gliocladium aureum* IFO 9055 was inoculated to each flask. The inoculated flask was incubated of a rotary shaker at 25° C. for 7 days.

A 1 ml portion of each culture was taken into a sterile test tube of 34 ml capacity, and after hermetic closure, incubated on a reciprocating shaker at 25° C. for 5 hours to cause evolution of a biogas. A 1 ml portion of the gas was taken from the top plenum of the tube with a gas syringe and subjected to gas chromatography and the production rate of $C_3$ and/or $C_4$ hydrocarbon was calculated as described in the text.

It was found that in the case of *Aspergillus clavatus* IFO-4045, the rate of production of propane is 0.1 nl/ml.hr. and that in the case of *Gliocladium aureum* IFO-9055, the rates of production of propane and n-butane are 0.2 nl/ml.hr. and 0.1 nl/ml.hr., respectively.

EXAMPLE 3

The three strains of *Aspergillus clavatus* IFO-4045, *Bacillus pumilus* IFO-3813 and *Actinomyces aurigineus* IFO-13022 were cultivated on the slants of agar (1.5 w/v %)-NB medium for fungi, bacteria and actinomycetes indicated in Table 1, and sterile distilled water was aseptically added to the cultures to give cell suspensions.

Five hundred ml of the NB media for fungi, bacteria and acinomycetes shown in Table 1 was added to 3 liter capacity Sakaguchi flask, respectively and after steam sterilization by autoclaving at 120° C. for 15 minutes and cooling, the above cell suspensions were inoculated to each flask. The pre-culture of the fungus was conducted at 25° C. for 3 days, that of the bacterial strain at 30° C. for 1 day, and that of the actinomycetes at 25° C. for 2 days, using a reciprocating shaker.

Jar fermentors of 14 liter capacity were charged with 10 liter of the NB media for fungi, bacteria and actinomycetes, respectively. After steam sterilization under pressure at 120° C. for 20 minutes and cooling, the above pre-cultures were inoculated to each jar fermentor. The fermentation of the fungus was conducted at 25° C. for 6 days, that of the bacterial strain at 30° C. for 2 days, and the actinomycetes at 25° C. for 5 days, under aeration with sterile air at $0.1^{VVM}$ and at 200 to 300 r.p.m. (the r.p.m. was adjusted according to the degree of foaming).

Throughout the fermentation period, the gases discharged from each jar fermentor were independently passed through a 10% NaOH bottle, a washing water bottle and a moisture separating bottle;, followed by serial passage through Molecular Sieves 3A, 4A and 5A [Union Showa K.K.] columns and the hydrocarbon adsorbed on Molecular Sieves 5A were desorbed and recovered under vacuum suction.

The hydrocarbons of 3 and/or 4 carbon atoms thus obtained were 1.0 mg of propane in the case of *Aspergillus clavatus* IFO-4045, 0.3 mg of 1-butene in the case of *Bacillus pumilus* IFO-3813, and 0.2 mg of n-butane in the case of *Actinomyces aurigineus* IFO-13022.

We claim:

1. A method for producing a hydrocarbon product having from 3 to 4 carbon atoms which consists essentially of inoculating a biologically pure strain of microorganism capable of producing the hydrocarbon product to a liquid medium containing nutrient sources, cultivating aerobically the strain in the liquid medium under aerated stirring thereby causing directly the formation of at least 0.1 nl/mlhr the hydrocarbon product in the culture liquid and in the gaseous phase of the culture, and recovering the hydrocarbon product from the liquid or gaseous phase, said strain of microorganism being a member selected from the group consisting of *Phytophtora capsici, Mucor hiemalis f. corticolus, Mucor hiemalis f. hiemalis, Mucor hiemalis f. luteus, Rhizopus javanicus, Rhizopus japonicus, Absidia cylindrospora, Mortierella isabellina, Mortierella elongata, Cunninghamerlla elegans, Taphrina caerulescens, Taphrina wiesneri, Monascus anka, Monascus albidus, Nectria flammea, Gibberella fujikuroi, Chaetomium globosum, Neurospora crassa, Monilia geophila, Trichoderma viride, Aspergillus clavatus, Paecilomyces carneus, Paecilomyces elegans, Gliocladium aureum, Gliocladium deliquescens, Gliocladium roseum, Sporotricum aureum, Microsporum gypseum, Trichophyton mentagrophytes, Cladosporium resinae, Syncephalastrum racemosum, Phycomyces nitens, Endomyces geotrichum, Endomyces reessii, Endomyces magnusii, Schizosaccharomyces octosporus, Schizosaccharomyces pombe, Schizosaccharomyces japonicus, Saccharomyces bailii,* Saccharomyces sp. IFO-2363, IFO-2226, IFO-2112, IFO-2115, IFO-2342, IFO-2343, IFO-2344, IFO-2345, IFO-2346, IFO-2347 or IFO-2376, *Pichia farinosa, Hansenula capsulata, Debaryomyces nepalensis, Saccharomycopsis lipoliitica, Saccharomycopsis crataegensis, Saccharomycopsis fibuligera, Rhodotorula glutinis, Rhodotorula minuta, Sporobolomyces salmonicolor, Sporobolomyces pararoseus, Cryptococcus albidus, Cryptococcus flavus, Cryptococcus laurentii, Candida albicans, Candida butyri, Candida guilliermondii, Brettanomyces bruxellensis, Brettanomyces intermedius, Bacillus circulans, Bacillus coagulans, Bacillus pumilus, Bacillus subtilis, Brevibacterium ammoniagenes, Brevibacterium lactofermentum, Corynebacterium aquaticum, Corynebacterium fascience, Corynebacterium paulometabolum, Micrococcus luteus, Paracoccus denitrificans, Proteus mirabilis, Pseudomonas aeruginosa, Pseudomonas putida, Pseudomonas stutzeri, Salmonella typhimurium, Serratia marcescens, Acetobacter aceti, Streptomyces flaveolus, Streptomyces fradiae, Streptomyces lavendulae, Streptomyces viridochromogenes, Streptomyces regensis, Actinomyces aurigineus, Actinomyces vulgaris, Amorphosporandium auranticolor,* or *Intrasporandium calvum.*

2. A method according to claim 1 wherein the liquid medium contains a reproducible biomass which is either naturally occurring or artificially available byproduct from forestal, fisheries or livestock industrial activities; industrial waste or waste water; or active sludges from the biological treatment of public sewage, plant effluent or raw sewage.

3. A method according to claim 1 wherein the strain is cultured aerobically in a liquid medium containing nutrient sources and inorganic salts at a pH of 2 to 9 and a temperature of 20° to 45° C. for 1 to 10 days, to thereby cause the formation of $C_3$ or $C_4$ hydrocarbon in the culture liquid and in the gaseous phase of the culture, and recovering the hydrocarbon from said liquid or gaseous phase.

4. A method according to claim 1 wherein the culture is carried out under aerated stirring in a liquid medium containing nutrient sources and inorganic salts, and the hydrocarbon is separated from the product biogas.

5. A method according to claim 1, wherein the hydrocarbon product is produced in the rate of 0.1–8.6 nl/ml.hr.

* * * * *